(12) United States Patent
Ninos et al.

(10) Patent No.: US 11,994,485 B2
(45) Date of Patent: May 28, 2024

(54) METHOD FOR OPERATING A GAS SENSOR DEVICE AND GAS SENSOR DEVICE

(71) Applicant: Robert Bosch GmbH, Stuttgart (DE)

(72) Inventors: Alexandros Ninos, Kusterdingen (DE); Thomas Claus, Leipzig (DE); Ye Lu, Reutlingen (DE); Christoph Brueser, Reutlingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 1053 days.

(21) Appl. No.: 16/763,143

(22) PCT Filed: Oct. 10, 2018

(86) PCT No.: PCT/EP2018/077580
§ 371 (c)(1),
(2) Date: May 11, 2020

(87) PCT Pub. No.: WO2019/096496
PCT Pub. Date: May 23, 2019

(65) Prior Publication Data
US 2020/0278310 A1     Sep. 3, 2020

(30) Foreign Application Priority Data
Nov. 13, 2017   (DE) .......................... 102017220114.2

(51) Int. Cl.
*G01N 27/12* (2006.01)
*G01N 27/14* (2006.01)
(Continued)

(52) U.S. Cl.
CPC ........... *G01N 27/124* (2013.01); *G01N 27/12* (2013.01); *G01N 27/14* (2013.01); *G01N 27/407* (2013.01);
(Continued)

(58) Field of Classification Search
CPC .. G01N 27/4077; G01N 27/12; G01N 27/407; G01N 33/0009; G01N 33/0031
(Continued)

(56) References Cited

U.S. PATENT DOCUMENTS

| 4,670,405 A | * | 6/1987 | Stetter | ................ G01N 33/0031 |
| | | | | 436/151 |
| 7,607,823 B2 | * | 10/2009 | Kent | ..................... G01M 3/002 |
| | | | | 374/185 |

(Continued)

FOREIGN PATENT DOCUMENTS

| CN | 1896731 A | 1/2007 |
| CN | 103140819 A | 6/2013 |

(Continued)

OTHER PUBLICATIONS

Javier Burgues et al., discontinuously operated MOX sensors for low power applications, 2017 ISOCS/IEEE International Symposium on Olafaction and Electronic Nose (ISOEN), May 2, 2017 (May 2, 2017), pp. 1-3 (Year: 2017).*

(Continued)

*Primary Examiner* — Stephanie E Bloss
*Assistant Examiner* — Kevin C Butler
(74) *Attorney, Agent, or Firm* — NORTON ROSE FULBRIGHT US LLP; Gerard A. Messina

(57) ABSTRACT

A method for operating a gas sensor device, which is equipped with at least one gas-sensitive electrical sensor resistor, a heating element for the controlled heating of the sensor resistor, a detection element for detecting the resistance value of the sensor resistor, and a signal processing element for processing measuring signals. In the method, measurements are carried out in time intervals, in which the resistance value of the sensor resistor is detected as a measuring signal, and the sensor resistor is heated for each (Continued)

measurement, the heating element being operated discontinuously in heating intervals and each measurement being assigned a heating interval. Measurements are automatically carried out in predefinable time intervals, and additional measurements are initiatable at arbitrary times. The duration of the heating intervals assigned to the individual measurements being selected as a function of the time interval to the preceding heating interval.

7 Claims, 6 Drawing Sheets

(51) Int. Cl.
*G01N 27/407* (2006.01)
*G01N 33/00* (2006.01)

(52) U.S. Cl.
CPC ..... *G01N 27/4077* (2013.01); *G01N 33/0009* (2013.01); *G01N 33/0031* (2013.01)

(58) Field of Classification Search
USPC .................................................. 73/31.05
See application file for complete search history.

(56) References Cited

U.S. PATENT DOCUMENTS

| | | | | |
|---|---|---|---|---|
| 8,117,894 | B2* | 2/2012 | Abdullah | G01N 27/122 340/634 |
| 8,459,097 | B2* | 6/2013 | Neff | G01N 27/4141 73/23.31 |
| 9,228,967 | B2* | 1/2016 | Alepee | G01N 27/128 |
| 10,598,645 | B2* | 3/2020 | Kao | G01N 33/0016 |
| 11,187,686 | B2* | 11/2021 | Egli | G01N 27/403 |
| 2007/0012565 | A1* | 1/2007 | Suzuki | G01N 27/124 204/424 |
| 2008/0136651 | A1* | 6/2008 | Li | G08B 29/183 340/589 |
| 2010/0083122 | A1* | 4/2010 | Kozloski | G06F 3/038 715/737 |
| 2010/0089122 | A1* | 4/2010 | Abdullah | G01N 27/122 73/25.05 |
| 2014/0260545 | A1* | 9/2014 | Ruhl | G01N 27/124 73/31.05 |
| 2015/0001095 | A1* | 1/2015 | Fix | G01N 27/12 204/406 |
| 2016/0216227 | A1* | 7/2016 | Boni | G01N 33/004 |
| 2018/0038825 | A1* | 2/2018 | Ratto | G01N 33/497 |
| 2020/0278310 | A1* | 9/2020 | Ninos | G01N 27/124 |
| 2021/0278383 | A1* | 9/2021 | Koller | G01N 33/0016 |
| 2021/0293733 | A1* | 9/2021 | Ninos | G01N 33/0027 |
| 2022/0187179 | A1* | 6/2022 | Zimmer | G01N 11/02 |
| 2023/0010457 | A1* | 1/2023 | Hildebrand | G06F 30/27 |

FOREIGN PATENT DOCUMENTS

| | | | | |
|---|---|---|---|---|
| CN | 104535623 | A | | 4/2015 |
| CN | 104541161 | A | | 4/2015 |
| CN | 106053546 | A | | 10/2016 |
| DE | 3507386 | A1 | | 9/1985 |
| DE | 102006025249 | A1 | | 12/2007 |
| DE | 102006025249 | A1 | * | 12/2007 ........... G01N 27/122 |
| DE | 102008054752 | A1 | * | 6/2010 ......... G01N 27/4141 |
| DE | 102008054752 | A1 | | 6/2010 |
| DE | 102010042013 | A1 | * | 4/2012 ........... F01N 11/007 |
| DE | 102014103429 | A1 | | 9/2014 |
| DE | 102013212478 | A1 | * | 12/2014 ............ G01N 27/12 |
| EP | 3082011 | A1 | * | 10/2016 .......... G01N 27/123 |
| JP | H04361148 | A | | 12/1992 |
| JP | 2000283943 | A | | 10/2000 |
| JP | 2000283943 | A | * | 10/2000 |
| JP | 3144427 | B2 | | 3/2001 |
| JP | 3144427 | B2 | * | 3/2001 |
| JP | 2007024539 | A | * | 2/2007 ......... F02D 41/1494 |

OTHER PUBLICATIONS

Dinko Oletic et al., 'Energy-efficient atmospheric CO concentration sensing with on-demand operating MOX gas sensor', IEEE Sensors 2014 Proceedings, Nov. 2, 2014 (Nov. 2, 2014), pp. 795-798 (Year: 2014).*
International Search Report for PCT/EP2018/077580, dated Dec. 20, 2018.
Javier Burgues et al., "Discontinuously Operated MOX Sensors for Low Power Applications", 2017 ISOCS/IEEE International Symposium on Olfaction and Electronic Nose (ISOEN), 2017, pp. 1-3. XP055530658.
Dinko Oletic et al., "Energy-Efficient Atmospheric CO Concentration Sensing With On-Demand Operating MOX Gas Sensor", IEEE Sensors 2014 Proceedings, 2014, pp. 795-798. XP055530659.
Netatmo Weather Station, (2012) http://www.produktinfo.vonrad.com/datenblaetter/600000-624999/615765-an-01-de-MACLAND_NETATMO_URBAN_WETTERSTATION.pdf, [accessed Jun. 7, 2018], pp. 1-28.
Air Quality Sensor AS-MLV-P2 Datasheet [v1-01], (2015) http://www.netzmafia.de/skripten/hardware/RasiPi/Projekt-Raumluftsensor/AS-MLVP2_Datasheet_EN_v2.pdf [accessed Jun. 7, 2018], pp. 1-24.
Prof. Juergen Plate: "REHAU Room Air Sensor, Raspberry-Pi-Project", (2017), http://web.archive.org/web/20171023201254/www.netzmafia.de/skripten/hardware/TasPi/Projekt-Raumlufsensor/index.html; pp. 1-7.
Baranov, et al.: "Optimization of power consumtion for gas sensor nodes: A survey," Sensors and Actuatiors A: Physical, 233 (2015), pp. 279-289.

* cited by examiner

METHOD FOR OPERATING A GAS SENSOR DEVICE AND GAS SENSOR DEVICE

FIELD

The present invention relates to a method for operating a gas sensor device. The present invention further relates to a gas sensor device.

BACKGROUND INFORMATION

To monitor the air quality in buildings, gas sensors may be installed, which carry out measurements at regular time intervals. Gas sensors measure the change of physical or chemical variables as a function of the surrounding medium. Thus, for example, a gas sensor including a field effect transistor is described in German Patent Application No. DE 10 2008 054752 A1, the gases to be detected diffusing into a gas-sensitive layer, which causes a change in potential at the field effect transistor. By measuring the currents or voltages at the outputs of the field effect transistor, it is possible to deduce the type and the properties of the surrounding gas.

The electrical resistance of the sensitive layer may change due to adsorption as a function of the components of the surrounding gas. Thus, the concentration of the reducing or oxidizing gas, the air moisture and the ambient temperature may be inferred by measuring the electrical resistance value. Measurements of the change in air quality are possible as a result.

Since volatile organic compounds in particular cause measurable changes of the concentration only at higher temperatures of approximately 300 to 400 degrees, the sensitive layer is heated during or before the measurements.

To obtain comparable measuring results, the time intervals between various measurements are usually constant. In order to save energy, a measurement is carried out merely every 5 minutes, for example. During the intervening idle period, the sensitive layer is not heated. Frequently, however, it is desirable to be able to interpose additional measurements. A user may, for example, open a window and wish to measure the effects on the air quality. The user in general will not be reasonably expected to have to wait up to 5 minutes. The chemical state of the sensitive layer of the gas sensor will differ, however, at the point in time of the additional measurement from the chemical state at the end of the regular idle period, which hampers the comparability of the measuring results.

SUMMARY

The present invention provides a method for operating a gas sensor device and a gas sensor device.

According to a first aspect of the present invention, the present invention provides an example method for operating a gas sensor device. The gas sensor device includes at least one gas-sensitive electrical sensor resistor, a heating element (heater) for the controlled heating of the sensor resistor, a detection element (detector) for detecting the resistance value of the sensor resistor and a signal processing element (signal processor) for processing measuring signals. Measurements are carried out in time intervals, in which the resistance value of the sensor resistor is detected as a measuring signal. The sensor resistor is heated for each measurement, the heating element being operated intermittently in heating intervals and each measurement being assigned a heating interval. Measurements are carried out automatically in predefinable time intervals, additional measurements being initiatable at arbitrary times. The duration of the heating intervals assigned to the individual measurements is selected as a function of the time interval from the preceding heating interval.

According to a second aspect of the present invention, the present invention provides an example gas sensor device including at least one gas-sensitive electrical sensor resistor, including a heating element for the controlled heating of the sensor resistor, including a detection element for detecting the resistance value of the sensor resistor, including a signal processing element for processing signals and including a control unit for activating the heating element, the detection element and the signal processing element for carrying out automatic and externally initiated measurements, the control unit being equipped with at least one interface for receiving external control signals.

Preferred specific embodiments of the present invention are described herein.

The present invention makes it possible to carry out additional measurements between two automatic measurements. In the event a user wishes to discover the influence of particular actions on the air quality, he/she may be immediately provided the corresponding information by carrying out an additional measurement. The user need therefore not wait until the subsequent automatic measurement, but may obtain the desired information immediately.

In order to nevertheless obtain comparable measuring results, the duration of the heating intervals assigned to the individual measurements are adapted or shortened. If, for example, the additional measurement is to be carried out shortly after a preceding automatic measurement, then the chemical state of the gas-sensitive electrical sensor resistor has not yet reached the state of equilibrium at the end of a regular idle period between two automatic measurements. However, by dynamically adapting the duration of the heating interval assigned to the additional measurement, the sensor resistor is heated preferably only until a chemical state is reached, which corresponds essentially to the chemical state of the sensor resistor at the end of a regular heating interval, i.e., at the end of a heating interval assigned to an automatic measurement, if no additional measurement is carried out.

Conversely, if the additional measurement is carried out shortly before a subsequent automatic measurement, then by dynamically adapting the duration of the heating interval assigned to the subsequent automatic measurement, the sensor resistor may be heated during the subsequent automatic heating interval until the chemical state of the sensor resistor again corresponds to the chemical state after the end of an automatic heating interval without a preceding additional measurement.

By dynamically adapting or reducing the heating times, it is possible to ensure the comparability of the measurements.

According to one preferred refinement of the example method according to the present invention, the automatic measurements are carried out in regular, predefined, in particular, identical time intervals, regardless of whether an additional measurement is initiated. Thus, the automatic measurements take place at fixed predefinable points in time, which are not a function of the presence of an additional measurement. The time intervals between two automatic measurements may preferably be constant, may be 5 minutes, for example.

According to one preferred refinement of the example method according to the present invention, the automatic measurements are carried out in regular, predefined, in particular, identical time intervals until an additional measurement is initiated. The next automatic measurement after an initiated additional measurement is carried out in a time interval that corresponds to the regular predefined time interval between two automatic measurements, if at least one further additional measurement is not initiated beforehand. The interval between an additional measurement and a subsequent automatic measurement is therefore identical to the interval that would have been set in the absence of the additional measurement between this subsequent automatic measurement and the preceding measurement. Thus, the additional measurement results in a shift in the times of the automatic measurements. Since the interval between the additional measurement and the subsequent automatic measurement corresponds to a regular time interval, only an adaptation of the duration of the heating interval assigned to the additional measurement is required. The duration of the heating interval assigned to the subsequent automatic measurement need not be adapted.

According to one preferred refinement of the example method according to the present invention, the sensor resistor is heated to a predefinable operating temperature at least in the heating intervals assigned to one measurement. The operating temperature is preferably constant, i.e., identical for all measurements. In this way, comparable measuring conditions may be achieved.

According to one preferred refinement of the example method according to the present invention, the resistance value of the sensor resistor is detected as a measuring signal during the heating interval assigned to the measurement. The resistance value may be detected during the heating interval itself or shortly after the heating interval, but is ascertained preferably at the end of the heating interval, as a result of which energy is saved, since an unnecessary heating is avoided.

According to one preferred refinement of the example method according to the present invention, the duration of the heating intervals assigned to the individual measurements are selected as a function of the time interval from the preceding heating interval in such a way that essentially the same measuring signal is detected in measurements under essentially constant ambient conditions. With the measurement conditions invariably the same as a result, the measured resistance values are comparable with one another regardless of whether or not an additional measurement takes place.

According to one preferred refinement of the example method according to the present invention, the dependency of the duration of the heating intervals on the time interval from the respectively preceding heating interval is determined on the basis of calibration measurements, which are carried out in a calibration step under essentially constant ambient conditions. Thus, in the event of a change in the ambient conditions, the comparability of the measured resistance values may again be ensured by adapting the duration of the heating intervals.

The calibration step includes preferably at least one measurement as a reference measurement and at least one calibration measurement in a predefinable time interval. The sensor resistor is heated for each calibration measurement at least until the resistance value of the sensor resistor corresponds to the resistance value of the reference measurement. For each calibration measurement, the duration until the resistance value of the reference measurement is reached and the time interval from the preceding heating interval are detected as calibration data.

The calibration step may be selectively activatable. Thus, for example, an initial calibration may be carried out during manufacture after the production of the gas sensor device under predefined ambient conditions, for example, in a clean room, in order to ascertain the correlation between the duration of the heating intervals assigned to the individual measurements and the time interval from the preceding heating interval. This correlation may be subsequently stored in a look-up table. The duration of the heating intervals may be ascertained during the operation with the aid of the look-up table. It is also possible for a user to activate the calibration step, for example, in the event the gas sensor device is exposed to changed ambient conditions.

According to one preferred refinement of the example method according to the present invention, the calibration step is activated automatically if an essentially identical measuring signal has been detected for a predefined number of successive automatic measurements. A constant measuring signal is an indication that the influences of changes of the ambient conditions may be disregarded. The essentially constant measuring signal may thus be used as a reference measurement.

The general dependency of the duration of a heating interval assigned to an individual measurement may be determined by interpolating the values ascertained in the calibration step. For example, the time difference between two automatic measurements, for example, 300 seconds, is divided into a plurality of smaller time differences, for example, of the duration of one second, two seconds or five seconds. An additional measurement is then carried out between a first and a second automatic measurement after the smaller time difference, i.e., for example, after a second, and the duration of the corresponding heating interval is ascertained. A further additional measurement is carried out between the second automatic measuring point in time and a subsequent third automatic measuring point in time after double the smaller time difference, i.e., for example, after two seconds, and the duration of the corresponding heating interval is again ascertained. Thus, the durations of the corresponding heating intervals are ascertained successively for various time differences between an automatic measurement and an additional measurement. The general dependency may be determined through interpolation.

According to one refinement of the example method according to the present invention, a plausibility check of the ascertained dependency may be carried out. Thus, for example, the dependency of the durations of the heating intervals on the time intervals obtained may be rejected in the event the durations of the heating intervals do not steadily increase with the time interval. In other words, the dependency of the durations of the heating intervals obtained is used for determining the corresponding durations of the heating intervals only if the duration of the heating intervals is a steadily increasing function of the increasing time interval. Otherwise, the previous dependency is maintained. The reason is that the heating time required for reaching the desired chemical state increases with the increasing time difference from a previous automatic measurement. If this behavior is not reproduced, it may be that the measurements are not correct, for example, because the ambient conditions have changed in the interim.

According to one preferred refinement of the present invention, the duration of a heating interval assigned to one measurement is adapted exactly when the time interval from the preceding heating interval falls below a predefined initial threshold value.

BRIEF DESCRIPTION OF THE DRAWINGS

In all figures, identical or functionally identical elements and devices are provided with the same reference numerals.

DETAILED DESCRIPTION OF EXAMPLE EMBODIMENTS

Figure 1:
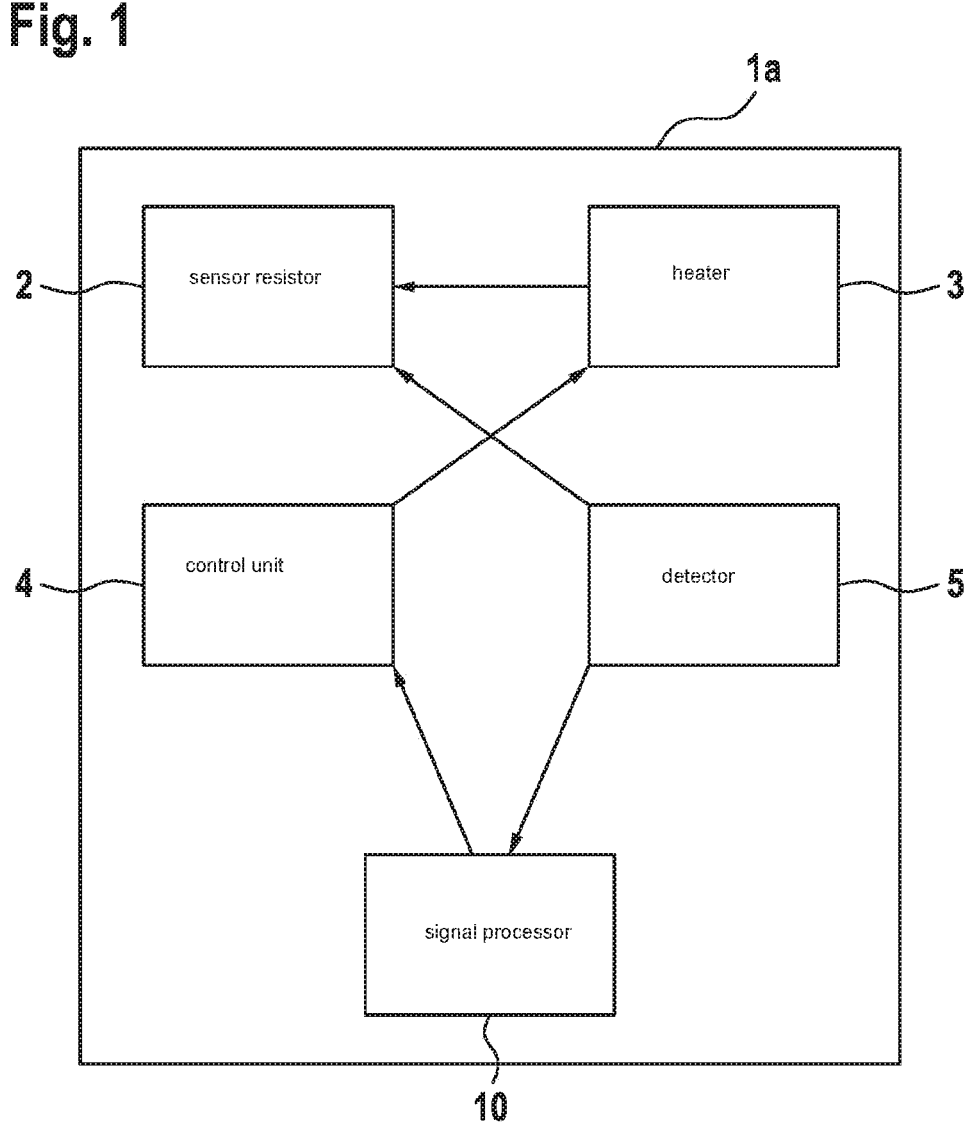
FIG. 1 shows a block diagram of a gas sensor device according to one specific embodiment of the present invention.

FIG. 1 shows a block diagram of a gas sensor device 1a according to one specific embodiment of the present invention. Gas sensor device 1a includes a gas-sensitive electrical sensor resistor 2, which may be designed, for example, as a layer including metallic-oxide semiconductor materials, for example, tin oxide $SnO_2$ or zinc oxide ZnO. Sensor resistor 2 need not necessarily have a layered design, however.

Gas sensor device 1a further includes a heating element 3, which is designed to heat sensor resistor 2. For this purpose, sensor resistor 2 may be heated to temperatures between 200 and 500 degrees and preferably between 300 and 400 degrees. Gas sensor device 1a further includes detection element 5, which measures an electrical resistance value R of sensor resistor 2.

To save energy, sensor resistor 2 is not continuously heated, rather heating element 3 and detection element 5 are activated with the aid of a control unit 4 of gas sensor device 1a in such a way that a heating of sensor resistor 2 is carried out by detection element 5 at regular heating points in time for one heating interval and one subsequent measurement of resistance value R. The resistance value is measured preferably at a measuring point in time at the end of every heating interval. Resistance values R together with the corresponding measuring points in time are detected as a measuring signal by signal processing element 10.

Figure 2:
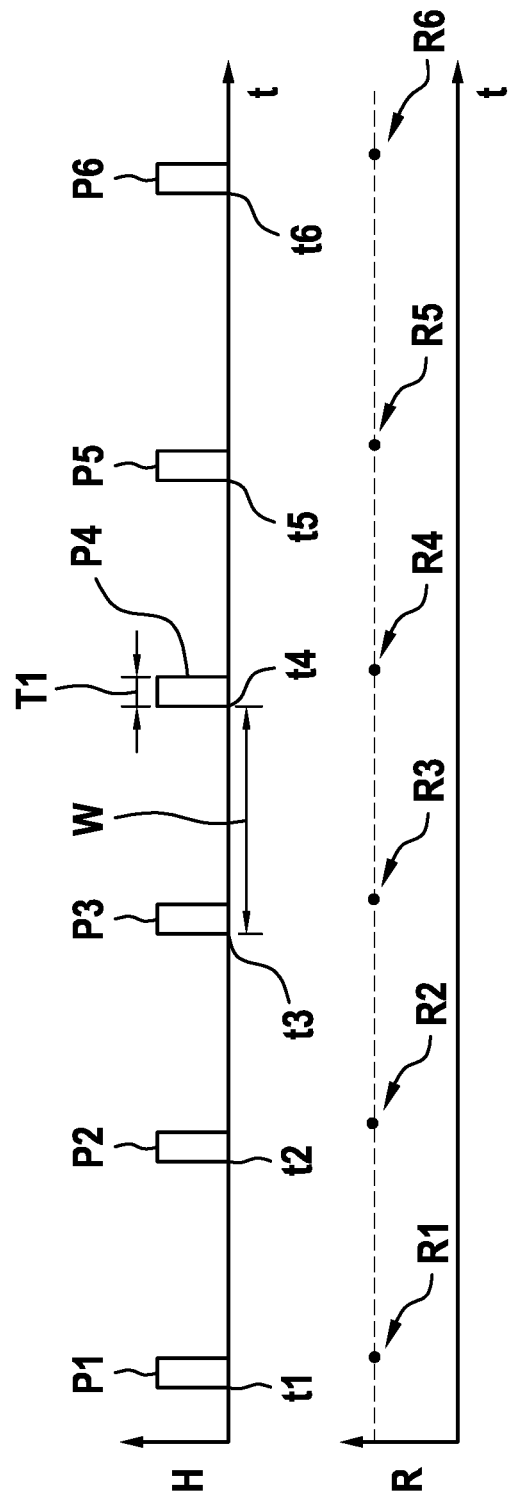
FIG. 2 shows an exemplary temporal sequence of heating intervals and corresponding resistance values.

As illustrated in FIG. 2, sensor resistor 2 is heated with the aid of heating element 3 at respective heating points in time t1 through t6 during respective heating intervals P1 through P6. A time difference W between two successive heating points in time t1 through t6 is preferably constant. The resistance value is measured in each case at the end of a heating interval P1 through P6, so that the time interval between two successive measurements corresponds to the time difference between two successive heating points in time t1 through t6. If the gas sensor device 1a is used for monitoring a room air quality, the time difference W may, for example, be between one and 10 minutes. Time difference W is preferably 300 seconds. Duration T1 of heating intervals P1 through P6 is also constant and, for example, is between one and five seconds. For example, duration T1 of the heating intervals may be 1.92 seconds.

Resistance value R measured at the end of every heating interval P is also illustrated in FIG. 2. If the ambient conditions of the gas sensor do not change, then corresponding resistance values R1 through R6 are essentially equal.

In the case of changing ambient conditions, resistance value R will change. Signal processing element 10 determines the presence of particular chemical components, or more generally, the humidity or air quality based on the measured resistance value or based on the change of the resistance value.

Control unit 4 is designed to receive a signal for carrying out an additional measurement. For this purpose, control unit 4 may have a user interface, so that a user may request an additional measurement directly at gas sensor device 1a. Control unit 4 may, however, also communicate with external devices via a wireless interface and may receive the signal from the external devices for carrying out the additional measurements.

Based on the signal, control unit 4 activates heating element 3 and detection element 5 so that sensor resistor 2 is additionally heated at an extra heating point in time t7, t8 for the duration of an additional heating interval, extra heating point in time t7, t8 being between two regular heating points in time t1 through t6. Extra heating point in time t7, t8 may take place immediately or at a predetermined time after the user input or after the signal is received. An additional measurement takes place by detection element 5 at the end of a respective additional heating interval, signal processing element 10 detecting the resistance value of sensor resistor 2 together with the point in time of the additional measurement as a measuring signal.

Figure 3:
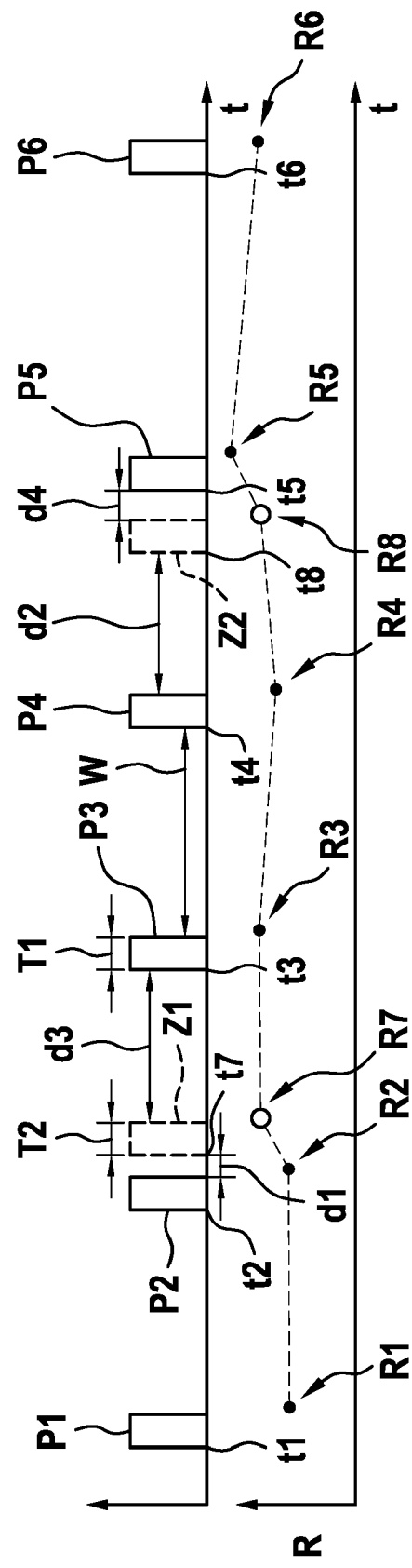
FIG. 3 shows temporal sequences of heating intervals and corresponding resistance values without dynamic adaptation of the durations of the heating intervals.

FIG. 3 illustrates how resistance value R would change if duration T2 of heating intervals Z1, Z2 were not adapted at respective extra points in time t7, t8, i.e., were selected equal to duration T1 of automatic heating intervals P1 through P6. In this case, sensor resistor 2 is heated too long so that under constant ambient conditions, resistance value R7, R8 is higher than resistance value R1, R2 during regular measurements without additional measurements. Moreover, the disruption of the chemical balance as a result of the additional measurements also impacts the subsequent automatic heating intervals P3, P5, P6, so that there as well, measured resistance values R3, R5, R6 turn out to be too high.

Figure 4:
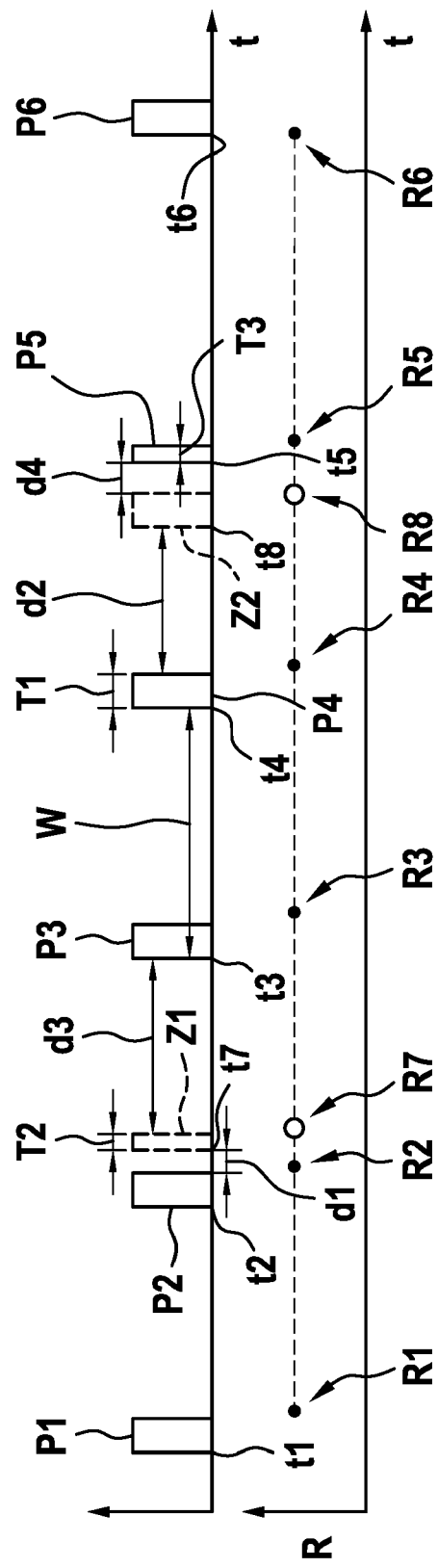
FIG. 4 shows temporal sequences of heating intervals and corresponding resistance values including the dynamic adaptation of the durations of the heating intervals according to the present invention.

Thus, according to the present invention, duration T2 of the heating intervals is adapted to predefined extra heating point in time t7 by control unit 4. As shown in FIG. 4, duration T2 is reduced in such a way that under constant ambient conditions, resistance value R7, which is measured at the end of additional heating interval Z1, is identical to resistance value R1 through R6 at the end of automatic heating intervals P1 through P6.

The adaptation is undertaken preferably if a time difference d1, d2 measured by control unit 4 between extra point in time t7, t8 and preceding heating interval P2, P4 is smaller than a predefined threshold value. Otherwise, duration T2 is selected to be equal to duration T1 of regular heating intervals P1 through P6.

An adaptation of a duration T3 of a regular heating interval P3, P5 following an extra heating point in time t7, t8 is also carried out if a time difference between extra heating point in time t7, t8 and the subsequent regular extra heating point in time t3, t5 is smaller than a predefined threshold value. Otherwise, duration T3 is selected to be equal to duration T1 of regular heating intervals P1 through P6. Duration T3 is set by control unit 4 in such a way that resistance value R5 measured at the end of heating interval P5 is equal to constant resistance value R1, R2 at the end of additional regular heating intervals P1, P2.

In the scenario illustrated in FIG. 4, an adaptation of duration T2 of additional heating interval Z1 takes place for extra heating point in time t7, whereas no adaptation of the duration of subsequent heating interval P3 takes place. Furthermore, an adaptation of subsequent heating interval P5 takes place for extra heating point in time t8, whereas no adaptation of additional heating interval Z2 itself takes place. However, the durations of both heating intervals Z1, Z2, or P3, P5 or the durations of none of the two heating intervals Z1, Z2, or P3, P5 may also be adapted as a function of time differences d1 through d4.

The heating points in time, which follow an additional measurement, may also be adapted. According to further specific embodiments, heating intervals may also occur that are not linked to any measurements.

Control unit 4 may adapt duration T2 of heating intervals Z1, Z2, as a function of a time difference d, to preceding heating interval P2, P4 using a look-up table.

Figure 5:
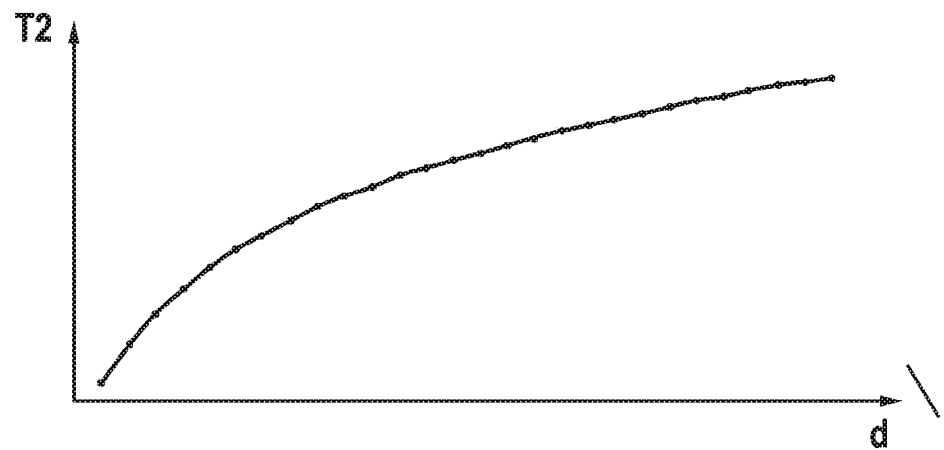
FIG. 5 schematically shows a dependency of the duration of the heating intervals on the time difference from the preceding heating interval.

FIG. 5 depicts an exemplary correlation between duration T2 of heating intervals Z1, Z2 and time difference d. To produce this correlation, resistance value R of sensor resistor 2 is continuously measured with the aid of detection element 5, the ambient conditions being held constant. Without extra measurements, resistance value R assumes a constant value R0 at the end of regular heating intervals P1 through P6. Heating element 3 is switched off, i.e., the heating of sensor resistor 2 is terminated, for a predefined time difference d precisely in the event resistance value R is equal to constant value R0. Corresponding duration T2 of heating interval Z1, Z2 is registered and assigned to time difference d. The correlation illustrated in FIG. 5 for different time differences d may be ascertained by repeated implementation. The ascertained measuring results may be preferably interpolated in order to obtain a continuous correlation.

According to one refinement of the present invention, the calibration just described may take place during the operation of gas sensor device 1a. In this way, gas sensor device 1a is able to carry out a self-calibration. The self-calibration is carried out preferably only if an essentially constant resistance value R0 is measured over a predefined time period, for example, several minutes, hours or even days. Control unit 4 then generates extra measuring points in time t7, t8, one extra measuring time t7, t8 at most being preferably between two regular measuring points in time t1, through t6. Heating element 3 heats the sensor resistor 2 until continuously measured resistance value R is equal to constant value R0. Measured duration T2 is assigned to corresponding time difference d. With repeated implementation, it is possible to ascertain the exact correlation between duration T2 and time difference d. The look-up table may be updated accordingly.

Figure 6:
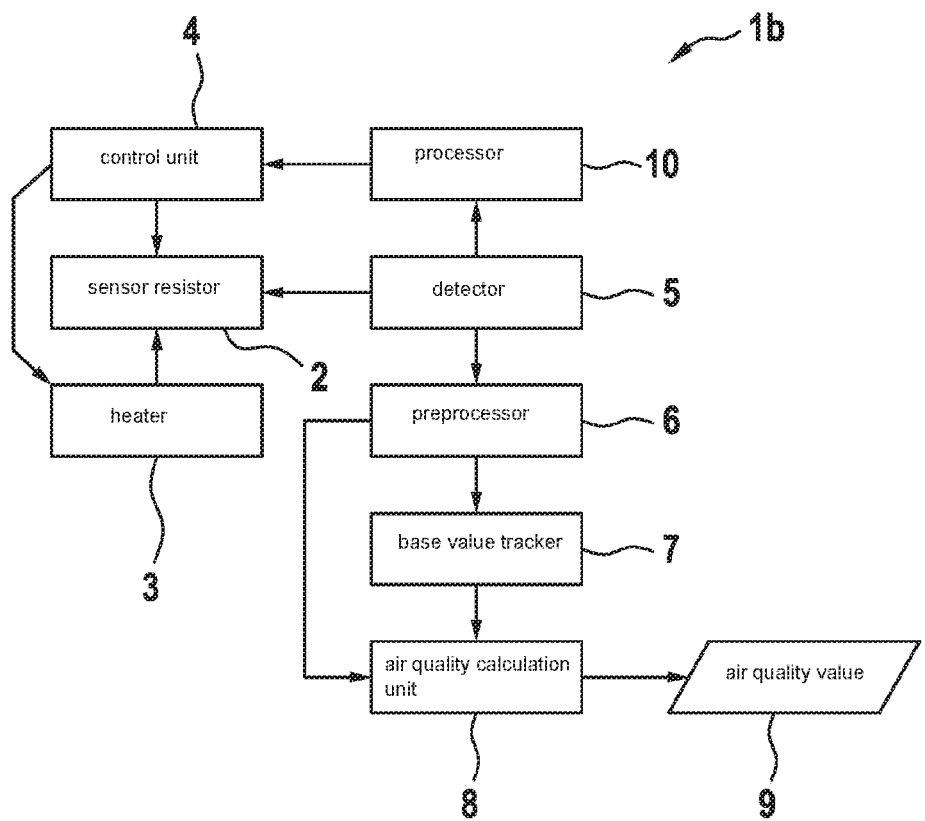
FIG. 6 shows a block diagram of a gas sensor device according to one specific embodiment of the present invention.

A block diagram of a gas sensor device 1b according to a further specific embodiment is illustrated in FIG. 6. In addition to the elements previously described above, whose mode of operation will not be repeated here, gas sensor device 1b includes a preprocessor 6, which is designed to preprocess resistance values R measured by detection element 5. A base value tracker 7 analyzes the preprocessed data over a longer time period and thus ascertains a base value. The base value may, for example, be equal to a maximum measured resistance value R, which corresponds to room air of high air quality, since few additional chemical components are present. This base value is used to calculate the air quality at an arbitrary point in time. For this purpose, an air quality calculation unit 8 compares measured resistance values R with the base value, thus compares the instantaneous air quality with the optimum air quality, and outputs an air quality value 9. This value may be displayed to a user via an interface.

Figure 7:
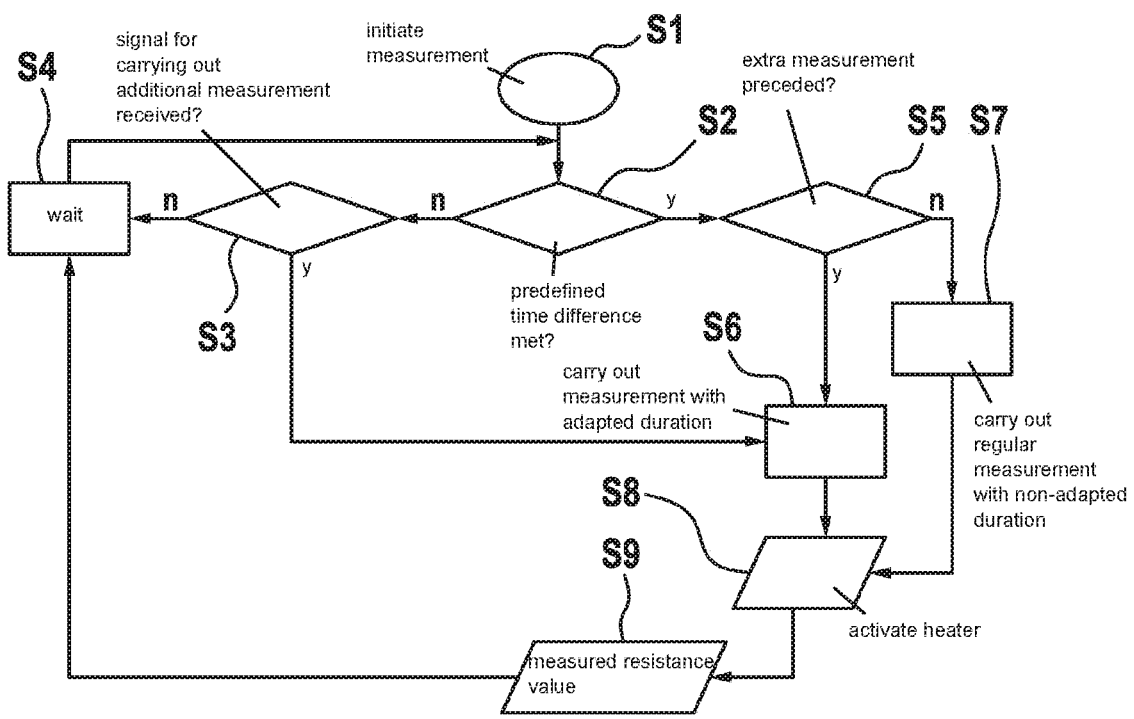
FIG. 7 shows a flow chart for explaining a method for operating a gas sensor device according to one specific embodiment of the present invention.

FIG. 7 shows a flow chart of a method for operating a gas sensor device 1, 1b, which may be one of the gas sensor devices 1, 1b described above. The measurement is initiated in a method step S1. In a method step S2, it is checked whether predefined time difference W between two regular measuring points in time t1 through t6, for example, 300 seconds, has already been reached. If this is not the case, it is checked in a method step S3 whether a signal for carrying out an additional measurement is received. If this is not the case, waiting ensues for a predefined period, for example, 3 seconds in a method step S4, and method step S2 is subsequently carried out again. If a signal for carrying out an additional measurement is received, a measurement with an adapted duration T2 of assigned heating interval Z1, Z2 is carried out in a method step S6.

If predefined time difference W is reached in method step S2, it is then checked in a method step S5 whether an extra measurement has preceded. If this is the case, a measurement with an adapted duration T3 of heating interval P5 is also carried out in method step S6. Otherwise, a regular measurement with a non-adapted duration T1 is carried out in a method step S7.

To carry out the measurement, heating element 3 is activated in a method step S8 for the respective determined duration of the heating interval and measured resistance value R is output in a method step S9.

According to further specific embodiments, the next automatic measurement may be carried out after an additional measurement in a time interval, which corresponds to the regular predefined time interval between two automatic measurements.

What is claimed is:

1. A method for operating a gas sensor device, the gas sensor device including at least one gas-sensitive electrical sensor resistor, a heater for a controlled heating of the sensor resistor, a detector configured to detect a resistance value of the sensor resistor, and a signal processor configured to process measuring signals, the method comprising the following steps:
   carrying out measurements in time intervals, in which the resistance value of the sensor resistor is detected as a measuring signal, and in which the sensor resistor is heated for each measurement, the heater being operated discontinuously in heating intervals and each of the measurements being assigned a respective heating interval;
   wherein:
     at least some of the measurements are carried out automatically in predefined time intervals, and additional ones of the measurements are initiatable at arbitrary times;
     a duration of each of the respective heating intervals assigned to individual ones of the measurements being selected as a function of a time interval from a respective preceding heating interval;
     the sensor resistor is heated to a predefined operating temperature at least in the respective heating intervals assigned to the measurements, the resistance value of the sensor resistor being detected, as the measuring signal during each of the respective heating intervals assigned to the measurements, at an end of the each of the respective heating intervals;

the duration of each of the respective heating intervals assigned to the individual ones of the measurements being selected as a function of the time interval to the respective preceding heating interval in such a way that the same measuring signal is detected in the measurements under constant ambient conditions; and a dependency of the duration of each of the heating intervals on the time interval from the respective preceding heating interval is determined based on calibration measurements, which are carried out in a calibration step under constant ambient conditions, wherein the sensor resistor is configured to be additionally heated for an additional heating interval.

2. The method as recited in claim 1, wherein the measurements that are carried out automatically are carried out in regular, predefined, identical time intervals, regardless of whether any of the additional measurements is initiated.

3. The method as recited in claim 1, wherein the measurements that are carried out automatically are carried in regular, predefined, identical time intervals until one of the additional measurements is initiated, and a next one of the measurement that are carried out automatically is carried out after an initiated one of the additional measurements in a time interval, which corresponds to the regular, predefined time interval between two automatic measurements if at least one further additional measurement is not initiated beforehand.

4. The method as recited in claim 1, wherein the calibration step includes at least one measurement as a reference measurement and at least one calibration measurement in a predefinable time interval, the sensor resistor being heated for each calibration measurement at least until the resistance value of the sensor resistor corresponds to the resistance value of the reference measurement, and, for each calibration measurement, a duration until the resistance value of the reference measurement is reached and a time interval to the preceding heating interval then being detected as calibration data.

5. The method as recited in claim 4, wherein the calibration step is optionally activated.

6. The method as recited in claim 1, wherein the calibration step is automatically activated when identical measuring signals have been detected for a predefined number of successive measurements that are carried out automatically.

7. A gas sensor device, comprising:
at least one gas-sensitive electrical sensor resistor;
a heater for a controlled heating of the sensor resistor;
a detector configured to detect a resistance value of the sensor resistor;
a signal processor configured to process measuring signals; and
a control unit configured to activate the heater, the detector, and to signal processor, to carry out automatic and externally initiated measurements, the control unit including at least one interface configured to receive external control signals;

wherein:
the sensor resistor is heatable to a predefined operating temperature by the heater at least in respective heating intervals assigned to individual ones of the measurements;

the detector is configured to detect the resistance value of the sensor resistor, as a measuring signal during the respective heating intervals assigned to the individual ones of the measurements, at the end of each of the respective heating intervals;

the control unit is configured to select a duration of the each of the respective heating intervals assigned to the individual ones of the measurements as a function of a time interval from a respective preceding heating interval in such a way that the same measuring signal is detectable in the measurements under constant ambient conditions; and the control unit is configured to determine a dependency of the duration of each of the heating intervals on the time interval from the respective preceding heating interval based on calibration measurements, which are implemented in a calibration step under constant ambient conditions, wherein the sensor resistor is configured to be additionally heated for an additional heating interval.

* * * * *